United States Patent [19]

Balkovec et al.

[11] Patent Number: 5,668,105
[45] Date of Patent: *Sep. 16, 1997

[54] AZA CYCLOHEXAPEPTIDE COMPOUNDS

[75] Inventors: James M. Balkovec, North Plainfield; Frances A. Bouffard, Scotch Plains; Milton L. Hammond, Somerville, all of N.J.

[73] Assignee: Merck & Co., Inc., Rahway, N.J.

[*] Notice: The term of this patent shall not extend beyond the expiration date of Pat. No. 5,378,804, and 5,514,650, and 5,514,651.

[21] Appl. No.: 614,452

[22] Filed: Mar. 12, 1996

Related U.S. Application Data

[63] Continuation-in-part of Ser. No. 307,979, Sep. 16, 1994, abandoned.

[51] Int. Cl.⁶ .............................. A61K 38/12; C07K 7/64
[52] U.S. Cl. .......................... 514/11; 514/9; 514/2; 530/317; 930/270; 930/DIG. 548; 930/DIG. 546
[58] Field of Search ................. 514/11, 9, 2; 530/317; 930/270, DIG. 548, DIG. 546

[56] References Cited

U.S. PATENT DOCUMENTS

| | | | |
|---|---|---|---|
| 5,021,341 | 6/1991 | Giacobbe et al. | 435/71.1 |
| 5,306,708 | 4/1994 | Schwartz et al. | 514/11 |
| 5,378,804 | 1/1995 | Balkovec et al. | 530/317 |

FOREIGN PATENT DOCUMENTS

| | | |
|---|---|---|
| 561639 | 9/1993 | European Pat. Off. . |

OTHER PUBLICATIONS

Walzer, et al., Diagn. Microbiol. Infect. Dis., vol. 2, pp. 1–6, 1984.

S. A. Morris et al., J. Antibiotics, vol. 47 (7), pp. 755–764 1994.

Zambias, et al., J. Medicinal Chemistry, vol. 35(15), pp. 2843–2855, 1992.

*Primary Examiner*—Ponnathapura Achutamurthy
*Assistant Examiner*—T. D. Wessendorf
*Attorney, Agent, or Firm*—Elliott Korsen; Mark R. Daniel

[57] ABSTRACT

Compounds represented by the formula (Seq ID Nos. 1–6)

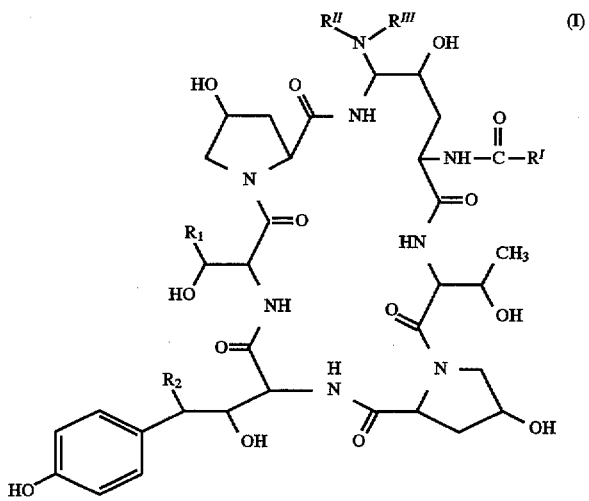

wherein all substituents are fully defined, are disclosed. These compounds exhibit utilities as antibiotic and antifungal agents and for the treatment and prevention of Pneumocystis infections.

3 Claims, No Drawings

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Xaa Thr Xaa Xaa Xaa Xaa
    1                    5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:2:

Xaa Thr Xaa Xaa Xaa Xaa
    1                    5

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:3:

Xaa Thr Xaa Xaa Xaa Xaa
    1                    5

( 2 ) INFORMATION FOR SEQ ID NO:4:

( i ) SEQUENCE CHARACTERISTICS:
    ( A ) LENGTH: 6 amino acids
    ( B ) TYPE: amino acid
    ( C ) STRANDEDNESS: unknown
    ( D ) TOPOLOGY: circular ( i i ) MOLECULE TYPE: peptide ( x i ) SEQUENCE DESCRIPTION: SEQ ID NO:4:

```
Xaa Thr Xaa Xaa Xaa Xaa
1               5
```

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:5:

```
Xaa Thr Xaa Xaa Xaa Xaa
1               5
```

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:6:

```
Xaa Thr Xaa Xaa Xaa Xaa
1               5
```

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:7:

```
Xaa Thr Xaa Xaa Xaa Xaa
1               5
```

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:8:

```
Xaa Thr Xaa Xaa Xaa Xaa
1               5
```

( 2 ) INFORMATION FOR SEQ ID NO:9:

( i ) SEQUENCE CHARACTERISTICS:
            ( A ) LENGTH: 6 amino acids
            ( B ) TYPE: amino acid
            ( C ) STRANDEDNESS: unknown
            ( D ) TOPOLOGY: circular ( i i ) MOLECULE TYPE: peptide ( x i ) SEQUENCE DESCRIPTION: SEQ ID NO:9:

Xaa Thr Xaa Xaa Xaa Xaa
1               5

( 2 ) INFORMATION FOR SEQ ID NO:10:

( i ) SEQUENCE CHARACTERISTICS:
            ( A ) LENGTH: 6 amino acids
            ( B ) TYPE: amino acid
            ( C ) STRANDEDNESS: unknown
            ( D ) TOPOLOGY: circular ( i i ) MOLECULE TYPE: peptide ( x i ) SEQUENCE DESCRIPTION: SEQ ID NO:10:

Xaa Thr Xaa Xaa Xaa Xaa
1               5

( 2 ) INFORMATION FOR SEQ ID NO:11:

( i ) SEQUENCE CHARACTERISTICS:
            ( A ) LENGTH: 6 amino acids
            ( B ) TYPE: amino acid
            ( C ) STRANDEDNESS: unknown
            ( D ) TOPOLOGY: circular ( i i ) MOLECULE TYPE: peptide ( x i ) SEQUENCE DESCRIPTION: SEQ ID NO:11:

Xaa Thr Xaa Xaa Xaa Xaa
1               5

( 2 ) INFORMATION FOR SEQ ID NO:12:

( i ) SEQUENCE CHARACTERISTICS:
            ( A ) LENGTH: 6 amino acids
            ( B ) TYPE: amino acid
            ( C ) STRANDEDNESS: unknown
            ( D ) TOPOLOGY: circular ( i i ) MOLECULE TYPE: peptide ( x i ) SEQUENCE DESCRIPTION: SEQ ID NO:12:

Xaa Thr Xaa Xaa Xaa Xaa
1               5

( 2 ) INFORMATION FOR SEQ ID NO:13:

( i ) SEQUENCE CHARACTERISTICS:
            ( A ) LENGTH: 6 amino acids
            ( B ) TYPE: amino acid
            ( C ) STRANDEDNESS: unknown
            ( D ) TOPOLOGY: circular ( i i ) MOLECULE TYPE: peptide ( x i ) SEQUENCE DESCRIPTION: SEQ ID NO:13:

Xaa Thr Xaa Xaa Xaa Xaa
1               5

( 2 ) INFORMATION FOR SEQ ID NO:14:

( i ) SEQUENCE CHARACTERISTICS:
    ( A ) LENGTH: 6 amino acids
    ( B ) TYPE: amino acid
    ( C ) STRANDEDNESS: unknown
    ( D ) TOPOLOGY: circular ( i i ) MOLECULE TYPE: peptide ( x i ) SEQUENCE DESCRIPTION: SEQ ID NO:14:

Xaa Thr Xaa Xaa Xaa Xaa
1               5

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:15:

Xaa Thr Xaa Xaa Xaa Xaa
1               5

( 2 ) INFORMATION FOR SEQ ID NO:16:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:16:

Xaa Thr Xaa Xaa Xaa Xaa
1               5

( 2 ) INFORMATION FOR SEQ ID NO:17:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:17:

Xaa Thr Xaa Xaa Xaa Xaa
1               5

( 2 ) INFORMATION FOR SEQ ID NO:18:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:18:

Xaa Thr Xaa Xaa Xaa Xaa
1               5

( 2 ) INFORMATION FOR SEQ ID NO:19:

( i ) SEQUENCE CHARACTERISTICS:
  ( A ) LENGTH: 6 amino acids
  ( B ) TYPE: amino acid
  ( C ) STRANDEDNESS: unknown
  ( D ) TOPOLOGY: circular ( i i ) MOLECULE TYPE: peptide ( x i ) SEQUENCE DESCRIPTION: SEQ ID NO:19:

Xaa Thr Xaa Xaa Xaa Xaa
1               5

( 2 ) INFORMATION FOR SEQ ID NO:20:

( i ) SEQUENCE CHARACTERISTICS:
    ( A ) LENGTH: 6 amino acids
    ( B ) TYPE: amino acid
    ( C ) STRANDEDNESS: unknown
    ( D ) TOPOLOGY: circular ( i i ) MOLECULE TYPE: peptide ( x i ) SEQUENCE DESCRIPTION: SEQ ID NO:20:

Xaa Thr Xaa Xaa Xaa Xaa
1               5

( 2 ) INFORMATION FOR SEQ ID NO:21:

( i ) SEQUENCE CHARACTERISTICS:
    ( A ) LENGTH: 6 amino acids
    ( B ) TYPE: amino acid
    ( C ) STRANDEDNESS: unknown
    ( D ) TOPOLOGY: circular ( i i ) MOLECULE TYPE: peptide ( x i ) SEQUENCE DESCRIPTION: SEQ ID NO:21:

Xaa Thr Xaa Xaa Xaa Xaa
1               5

( 2 ) INFORMATION FOR SEQ ID NO:22:

( i ) SEQUENCE CHARACTERISTICS:
    ( A ) LENGTH: 6 amino acids
    ( B ) TYPE: amino acid
    ( C ) STRANDEDNESS: unknown
    ( D ) TOPOLOGY: circular ( i i ) MOLECULE TYPE: peptide ( x i ) SEQUENCE DESCRIPTION: SEQ ID NO:22:

Xaa Thr Xaa Xaa Xaa Xaa
1               5

( 2 ) INFORMATION FOR SEQ ID NO:23:

( i ) SEQUENCE CHARACTERISTICS:
    ( A ) LENGTH: 6 amino acids
    ( B ) TYPE: amino acid
    ( C ) STRANDEDNESS: unknown
    ( D ) TOPOLOGY: circular ( i i ) MOLECULE TYPE: peptide ( x i ) SEQUENCE DESCRIPTION: SEQ ID NO:23:

Xaa Thr Xaa Xaa Xaa Xaa
1               5

( 2 ) INFORMATION FOR SEQ ID NO:24:

(   i   ) SEQUENCE CHARACTERISTICS:
    (  A  ) LENGTH: 6 amino acids
    (  B  ) TYPE: amino acid
    (  C  ) STRANDEDNESS: unknown
    (  D  ) TOPOLOGY: circular (   i   i   ) MOLECULE TYPE: peptide (   x   i   ) SEQUENCE DESCRIPTION: SEQ ID NO:24:

```
Xaa  Thr  Xaa  Xaa  Xaa  Xaa
1              5
```

AZA CYCLOHEXAPEPTIDE COMPOUNDS

RELATED APPLICATIONS

This is a continuation-in-part application of application Ser. No. 08/307,979, filed Sep. 16, 1994, abandoned.

BACKGROUND OF THE INVENTION

The present invention is directed to aza cyclohexapeptide compounds which may be useful as antifungal and anti-Pneumocystis agents.

There presently exists a need for antifungal and anti-Pneumocystis agents due to an increase in the number of isolates which are resistant to conventional agents. Additionally, conventional agents show somewhat high levels of toxicity which limit their usefulness. Lastly, the incidence of *Pneumocystis carinii* pneumonia is increasing, particularly in view of the susceptibility to the infection of immuno-compromised patients, such as those suffering from AIDS.

SUMMARY OF THE INVENTION

The compound of the present invention, Compound I (Seq. ID Nos. 1–6) is characterized in having a nitrogen attached to the cyclohexapeptide ring at the 5-carbon of the 4-hydroxyornithine component (hereinafter "C-5-orn") as well as a hydroxy group attached to the 4-position of the 5-membered ring of the proline component. The compound may be represented by the formula (I)

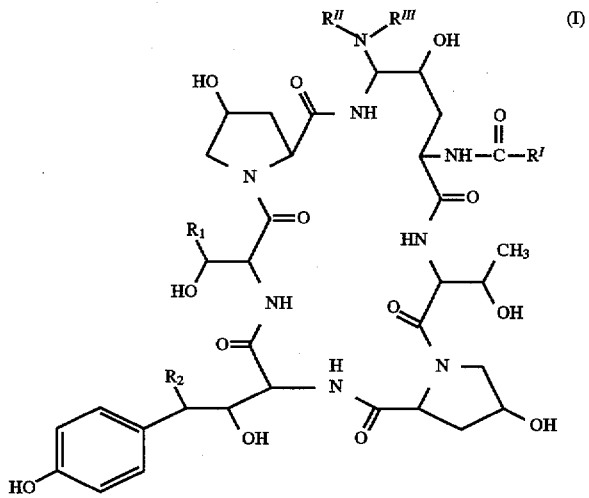

wherein
$R_1$ is $CH_2CH_2NH_2$, $CH_2CN$ or $CH_2CONH_2$;
$R_2$ is H or OH;
$R^I$ is $C_9$–$C_{21}$ alkyl or $C_9$–$C_{21}$ alkenyl;
$R^{II}$ is H, $C_1$–$C_4$ alkyl, $C_3$–$C_4$ alkenyl, $(CH_2)_{2-4}OH$, $(CH_2)_{2-4}NR^{IV}R^V$, $CO(CH_2)_{1-4}NH_2$;
$R^{III}$ is H, $C_1$–$C_4$ alkyl, $C_3$–$C_4$ alkenyl, $(CH_2)_{2-4}OH$, $(CH_2)_{2-4}NR^{IV}R^V$;
$R^{IV}$ is H or $C_1$–$C_4$ alkyl;
$R^V$ is H or $C_1$–$C_4$ alkyl; or a
pharmaceutically acceptable acid addition salt and/or hydrate thereof.

This invention also relates to pharmaceutical compositions containing said compounds and methods of use as antifungal agents and for the treatment and control of *Pneumocystis carinii* infections.

Particularly preferred is the compound wherein $R_1$ is $CH_2CH_2NH_2$; $R_2$ is OH; $R^I$ is 9,11-dimethyltridecyl; $R^{II}$ is $CH_2CH_2NH_2$; and $R^{III}$ is hydrogen.

Throughout the specification and appended claims, a given chemical formula or name shall encompass all optical and stereoisomers as well as racemic mixtures where such isomers and mixtures exist.

The term alkyl refers to straight, branched or cyclic chain hydrocarbon groups, e.g., methyl, ethyl, n-propyl, isopropyl, n-butyl, pentyl, hexyl, heptyl, cyclopentyl, cyclohexyl, cyclohexylmethyl and the like.

The term cycloalkyl refers to a species of alkyl containing from 3 to 15 carbon atoms without alternating or resonating double bonds between carbon atoms.

The term alkenyl refers to groups such as, e.g., vinyl, 1-propene-2-yl, 1-butene-4-yl, 2-buten-4-yl,1-pentene-5-yl and the like.

The term alkoxy refers to straight or branched chain oxyalkyl groups such as, e.g., methoxy, ethoxy, butoxy, heptoxy, dodecyloxy, and the like.

Pharmaceutically acceptable salts suitable as acid addition salts include salts of inorganic acid such as hydrochloric, hydrobromic, sulfuric, nitric, phosphonic and perchloric acids; as well as salts of organic acids such as tartaric, citric, acetic, succinic, maleic, fumaric and oxalic acids; as well as other substantially non-toxic acid addition salts which are known to those skilled in the art.

Representative nuclei for the aza derivatives of the present invention (Compound I) and the sequence ID for these compounds may be seen in the following table. Since the peptide nuclei would be the same irrespective of substituents $R^I$, $R^{II}$ or $R^{III}$, and since the sequence identification number is assigned for the nuclear variations, the amines and salts have the same sequence ID's.

| Aza Compound | $R_1$ | $R_2$ | SEQ ID NO. |
|---|---|---|---|
| I-1 | $CH_2CH_2NH_2$ | OH | 1 |
| I-2 | $CH_2CN$ | OH | 2 |
| I-3 | $CH_2CONH_2$ | OH | 3 |
| I-4 | $CH_2CH_2NH_2$ | H | 4 |
| I-5 | $CH_2CN$ | H | 5 |
| I-6 | $CH_2CONH_2$ | H | 6 |

The compounds are soluble in lower alcohols, and polar aprotic solvents such as dimethylformamide (DMF), dimethyl sulfoxide (DMSO) and pyridine. They are insoluble in solvents such as diethyl ether and acetonitrile.

The compounds of the present invention are useful as an antibiotic, especially as an antifungal agent or as an anti-protozoal agent. As antifungal agents they are useful for the control of both filamentous fungi and yeasts. They are especially adaptable to be employed for the treatment of mycotic infections in mammals, especially those caused by Candida species such as *C. albicans, C. tropicalis* and *C. pseudotropicalis*, Cryptococcus species such as *C. neoformans* and Aspergillus species such as *A. fumigatus, A. flavus, A. niger*. They are also useful for the treatment and/or prevention of *Pneumocystis carinii* pneumonia to which immune-compromised patients are especially susceptible as hereinafter described.

The compounds of the present invention may be prepared from the compound having the formula

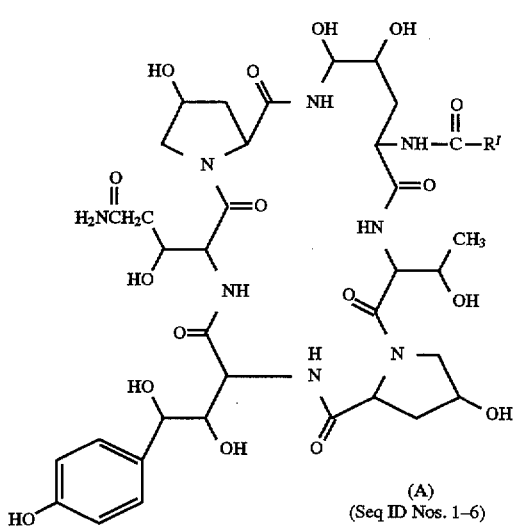

(A)
(Seq ID Nos. 1–6)

nitrogen. The starting material (Compound A) for the preparation may be a natural product in which $R^1$ is 9,11-dimethyltridecyl and may be produced by cultivating a mutagenized form of *Zalerion arboricola* ATCC 20868 as described in U.S. Pat. No. 5,306,708 which issued on Apr. 26, 1994.

The sequence IDs of the starting materials are seen in the following table:

| Compound | $R_1$ | $R_2$ | Starting Material SEQ ID NO. |
|---|---|---|---|
| A-1 | $CH_2CH_2NH_2$ | OH | 7 |
| A-2 | $CH_2CN$ | OH | 8 |
| A-3 | $CH_2CONH_2$ | OH | 9 |
| A-4 | $CH_2CH_2NH_2$ | H | 10 |
| A-5 | $CH_2CN$ | H | 11 |
| A-6 | $CH_2CONH_2$ | H | 12 | by a series of reactions in which the oxygen atom at the "C-5-orn" (or hemiaminal) position is ultimately replaced by nitrogen.

The sequence of reactions is shown in the following scheme.

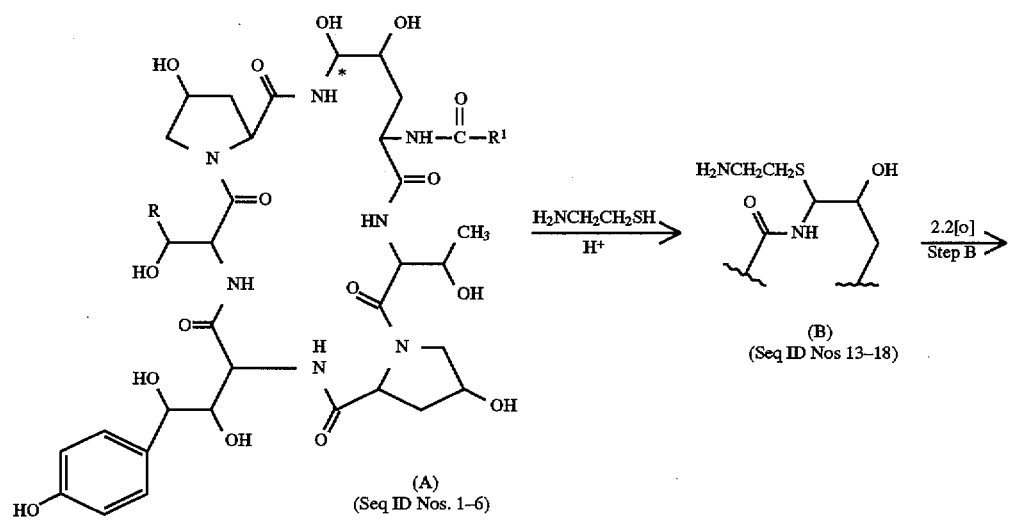

(A)
(Seq ID Nos. 1–6)

*The position is the "C-5-orn" or the hemiaminal position.

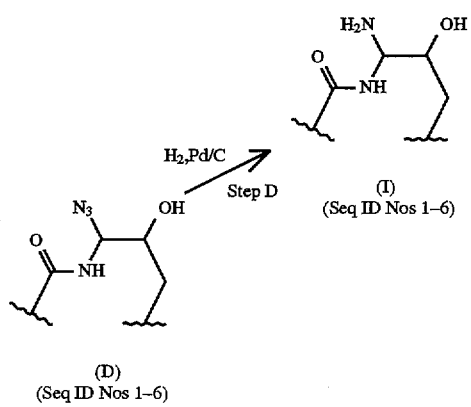

(D)
(Seq ID Nos 1–6)

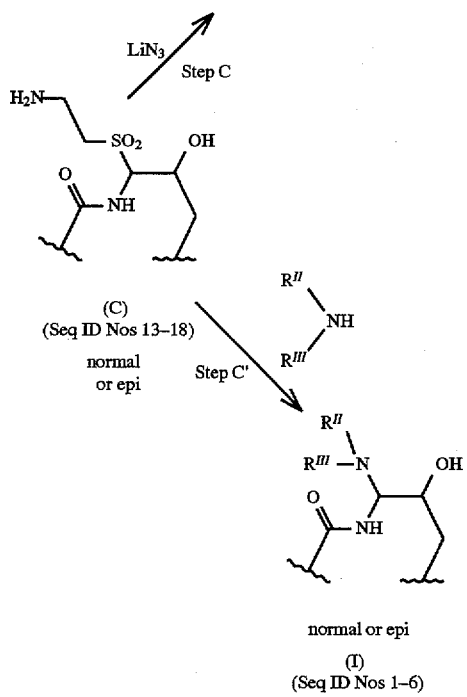

In Step A, the starting material Compound A (Seq ID Nos. 7–12), alkylthiol or arylthiol and acid are caused to react in an aprotic solvent under anhydrous conditions for time sufficient for reaction to take place with the formation of Compound B (Seq ID Nos. 13–18), seen in the following table. Aminoethylthiol has been found to be useful for this step.

| Compound | R₁ | R₂ | Sulfur Intermediate SEQ ID NO. |
|---|---|---|---|
| B-1 | CH₂CH₂NH₂ | OH | 13 |
| B-2 | CH₂CN | OH | 14 |
| B-3 | CH₂CONH₂ | OH | 15 |
| B-4 | CH₂CH₂NH₂ | H | 16 |
| B-5 | CH₂CN | H | 17 |
| B-6 | CH₂CONH₂ | H | 18 |

For Step A, suitable acids include strong organic acid and mineral acids. Examples of strong organic acids are camphorsulfonic acid, p-toluenesulfonic acid and methanesulfonic acid. Mineral acids include hydrochloric acid and hydrobromic acid. Camphorsulfonic acid is preferred.

Suitable solvents include DMF, DMSO, 1-methyl-2-pyrrolidinone and hexamethyl phosphoric triamide (HMPA). DMF or DMSO is preferred.

The reaction is generally carded out at ambient temperature for from 1 to about 10 days.

In carrying out the reaction, the cyclohexapeptide compound, the thiol compound and acid are stirred together in a suitable solvent until the reaction is substantially complete. The reaction mixture then is diluted with water and flash chromatographed on reverse phase resins using 10 to 40 percent acetonitrile/water (containing 0.1% trifluoroacetic acid) as eluant. Trifluoroacetic acid may hereinafter be designated "TFA". The fractions containing the desired product may be concentrated and lyophilized and the lyophilized material purified by preparative high performance liquid chromatography (HPLC).

Appropriate columns for HPLC are commercially available columns sold under trade mark names or trade names such as "ZORBAX" (DuPont), "DELTA PAK"; (Waters), BIO-RAD (Bio-Rad), "LICHROPREP" RP18 (E. Merck). The specific columns are identified in the working examples.

In Step B, Compound C (Seq ID Nos. 13–18), a sulfone is obtained by the oxidation of Compound B. Suitable oxidizing agents or oxidants include "OXONE," (KHSO₅·KHSO₄·K₂SO₄ 2:1:1, Aldrich Chemicals) metachloroperoxybenzoic acid, and peroxyacetic acid. The sequence ID of Compound C is the same as that of Compound B since the atom attached to the hemiaminal carbon is still sulfur. Thus, the sequence IDs of the sulfones are as follows:

| Compound | R₁ | R₂ | Sulfone SEQ ID No. |
|---|---|---|---|
| C-1 | CH₂CH₂NH₂ | OH | 13 |
| C-2 | CH₂CN | OH | 14 |
| C-3 | CH₂CONH₂ | OH | 15 |
| C-4 | CH₂CH₂NH₂ | H | 16 |
| C-5 | CH₂CN | H | 17 |
| C-6 | CH₂CONH₂ | H | 18 |

The oxidation of the thioether (Compound B) to the sulfone (Compound C) is carried out with about two molar amounts of the oxidant. When one molar amount of oxidant is employed, the product is a sulfoxide which may then be converted to the sulfone. The sulfoxides may be employed as an intermediate in the formation the aza compounds but the sulfone is preferred. A slight excess over the two molar amount of the oxidizing agent is employed.

The reaction is carried out in an aqueous medium, preferably a mixture of acetonitrile and water. About equal amounts are preferred although a range of 1:9 to 9:1 may be employed.

In carrying out the reaction, the oxidant is added to a solution of Compound B (Seq ID Nos. 13–18) in 1:1 acetonitrile/water and the mixture allowed to stand at ambient temperature for time sufficient to complete the reaction to obtain Compound C generally from about 30 minutes to one hour.

After completion of the reaction, the compound is recovered from the reaction mixture by diluting with water and chromatographing. Reverse phase (C18) flash column chromatography is suitable in this purification step. The preferred eluting agent is 30–45 percent acetonitrile/water (0.1% TFA) in 5 percent step gradients. The appropriate fractions are lyophilized to recover the desired sulfone intermediate, Compound C (Seq ID Nos. 13–18). The intermediate tends to be labile, thus the isolation should be carried out as rapidly as possible.

Compound C may be converted to a compound having a nitrogen directly attached to the "C-5-orn". As seen in the flow diagram, reaction of Compound C with an alkali metal azide produces an azide at that position (Compound D) while reaction with an amine compound (ammonia or amine) produces an amino group at the "C-5-orn" position, (Compound I). Compound D is an important intermediate for most of the compounds of the present invention. Although Compound D has nitrogen at "C-5-orn", since it is not a product, separate sequence ID Nos. are assigned for Compound D. Sequence ID Nos. for Compound D are found in the following table.

| Compound | $R_1$ | $R_2$ | Azide SEQ ID No. |
|---|---|---|---|
| D-1 | $CH_2CH_2NH_2$ | OH | 19 |
| D-2 | $CH_2CN$ | OH | 20 |
| D-3 | $CH_2CONH_2$ | OH | 21 |
| D-4 | $CH_2CH_2NH_2$ | H | 22 |
| D-5 | $CH_2CN$ | H | 23 |
| D-6 | $CH_2CONH_2$ | H | 24 |

The azide may be obtained by adding alkali metal azide while stirring at ambient temperature to a solution of the sulfone (Compound C, Seq. ID Nos. 13–18) in an aprotic solvent for time sufficient to complete the reaction with the formation of the azide as determined by HPLC analysis. The reaction mixture then may be diluted with aqueous acid such as trifluoroacetic acid and then chromatographed to separate the desired azide (Compound D) from the reaction mixture. Reverse-phase (C18) flash column chromatography using 10–25 percent acetonitrile/water (0.1% TFA) in 5 percent step gradients is suitable for this procedure.

The azide (Compound D) may then be reduced to a compound having a free amino group which is among the products (Compound I, Seq ID Nos. 1–6) of the present invention.

The reduction may be carried out by mixing the azide compound (Compound I) with Pd/C in a solvent such as glacial acetic acid and hydrogenating under balloon pressure for 10 to 20 hours. The product then may be recovered by first removing the catalyst by filtration and the filtrate lyophilized to obtain the amine compound (Seq ID Nos. 1–6) in which the amine is a primary amine.

The amine thus obtained may be converted into a substituted amine as subsequently described.

Compound I in which $-NR^{II}R^{III}$ is represented by $-NHCH_2CH_2NH_2$ or generically by $-NH(CH_2)_{2-4}NR^{IV}R^{V}$ may be prepared from the sulfone by a method in which a diamine $H_2N(CH_2)_{2-4}NR^{IV}R^{V}$ is caused to react with the sulfone (Compound C, Seq ID Nos. 13–18).

The reaction is carried out in an aprotic solvent such as those previously named and at ambient temperature. About tenfold molar excess of the amine compound is employed. The reaction may be carried out over one to several hours.

In carrying out the reaction, the appropriate amine is added to a solution of the sulfone in anhydrous aprotic solvent and the reaction mixture stirred at ambient temperature to obtain Compound I (Seq ID Nos. 1–6) in which the substituent at "C-5-orn" is $-NR^{II}R^{III}$. The desired compound may then be recovered by diluting with aqueous trifluoroacetic acid and then chromatographing. Reverse phase (C18) flash column chromatography eluting with 10 to 25% acetonitrile/water (0.1% TFA) in 5 percent step gradients is suitable. The appropriate fractions may be lyophilized to recover the product as a trifluoroacetate salt.

The trifluoroacetate salt may be converted by dissolving the salt in water and passing through a BIO-RAD AG2-X8 (Cl-) polyprep column and recovering the product as the hydrochloride salt.

The amines, prepared as above and having a primary amino group $-NH_2$ described, may then be alkylated by conventional means to obtain a substituted amino group. Briefly, alkylation may be carried out by causing an appropriately substituted alkyl halide to react with the amine (Compound I, $NR^{II}R^{III}$=$-NH_2$; Sequence ID Nos. 1–6) in an aprotic solvent in the presence of a base to obtain the monosubstituted amine (Compound I, $NR^{II}R^{III}$=$NHR^{II}$ wherein $R^{II}$ is $C_1$–$C_4$ alkyl, $C_3$–$C_4$ alkenyl, $(CH_2)_{2-4}OH$, and $(CH_2)_{2-4}NR^{IV}R^{V}$). The latter may be recovered from the reaction mixture by conventional procedures.

The amines, prepared as above described and having a primary amino group $-NH_2$, may be acylated by conventional means to obtain an acylated amino group. The acyl group contemplated is $CO(CH_2)_{1-4}NH_2$. Since this is a primary amino group, the amino of the acylating acid is protected such as with a benzyloxycarbonyl group before the acylation is carried out. An activated ester such as the pentafluorophenyl ester is preferably used. The acylation may be carried out in an aprotic solvent in the presence of base such as diisopropylethylamine at ambient temperature for from one to several hours to obtain the acylation product. The product may be recovered by diluting the reaction mixture with methanol and purifying by HPLC. The protecting group may be removed by conventional hydrogenolysis. (Compound I, $-NR^{II}R^{III}$=$-NHCO(CH_2)_{1-4}NH_2$).

The amine compounds in which the amino group at the hemiaminal position is totally substituted, i.e. when neither $R^{II}$ nor $R^{III}$ is

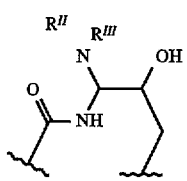

hydrogen, are preferably prepared by reacting the sulfone (Compound B, Seq ID Nos. 19-24) with an appropriately substituted amine $R^{II}R^{III}NH$. The reaction may be carried out by adding the amine to a stirred solution of the sulfone for time sufficient for reaction to take place. The product may be recovered by purifying by preparative HPLC and lyophilizing the appropriate components.

The invention also embraces acid addition salts. The compound in the normal course of isolation is obtained as an acid addition salt. Generally, it is as a trifluoroacetic acid salt. The salt thus obtained may be dissolved in water and passed through an anion exchange column bearing the desired anion. The eluate containing the desired salt may be concentrated to recover the salt as a solid product.

The compounds of the present invention are active against many fungi and particularly against Candida species. The antifungal properties may be illustrated with the minimum fungicidal concentration (MFC) determination against certain Candida organisms in a microbroth dilution assay carried out in a Yeast Nitrogen Base (DIFCO) medium with 1% dextrose (YNBD).

In a representative assay, compounds are solubilized in 100% dimethyl sulfoxide (DMSO) at an initial concentration of 5 mg/ml. Once dissolved, the drug stock is brought to a concentration of 512 µg/ml by dilution in water such that the final DMSO concentration was about 10 percent. The solution is then dispensed via a multichannel pipetter into the first column of a 96-well plate (each well containing 0.075 ml of YNBD), resulting in a drug concentration of 256 µg/ml. Compounds in the first column are diluted two-fold across the rows yielding final drug concentration ranging from 256 µg/ml to 0.12 µg/ml.

Four-hour broth cultures of organisms to be tested are adjusted using a spectrophotometer at 600 nm to equal a 0.5 McFarland Standard. This suspension is diluted 1:100 in YNBD to yield a cell concentration of $1-5 \times 10^4$ colony forming units (CFU)/ml. Aliquots of the suspension (0.075 ml) are inoculated into each well of the microtiter plate resulting in a final cell inoculum of $5-25 \times 10^3$ CFU/ml and final drug concentrations ranging from 128 µg/ml to 0.06 µg/ml. Each assay includes one row for drug-free control wells and one row for cell-free control wells.

After 24 hours of incubation, the microtiter plates are shaken gently on a shaker to resuspend the cells. The MIC-2000 inoculator is used to transfer a 1.5 microliter sample from each well of the 96-well microtiter plate to a single reservoir inoculum plate containing Sabouraud dextrose agar (SDA). The inoculated SDA plates are incubated for 24 hours at 35° C. and then read for minimum fungicidal concentration (MFC). MFC is defined as the lowest concentration of drug showing no growth or less than 4 colonies per spot.

The in vivo effectiveness of the compounds against fungi may be demonstrated in the following in vitro assay.

Growth from an overnight SDA culture of *C. albicans* MY 1055 is suspended in sterile saline and the cell concentration determined by hemacytometer count and the cell suspension adjusted to $3.75 \times 10^5$ cells/ml. Then 0.2 milliliter of this suspension is administered I.V. in the tail vein of mice so that the final inoculum is $7.5 \times 10^4$ cells/mouse.

The assay then is carried out by administering aqueous solutions of Compound I at various concentrations intraperitoneally (I.P.), twice daily (b.i.d.) for four consecutive days to 18 to 20 gram female DBA/2 mice, which previously had been infected with *C. albicans* in the manner described above. Distilled water is administered I.P. to *C. albicans* challenged mice as controls. After seven days, the mice are sacrificed by carbon dioxide gas, paired kidneys are removed aseptically and placed in sterile polyethylene bags containing 5 milliliters of sterile saline. The kidneys are homogenized in the bags, serially diluted in sterile saline and aliquots spread on the surface of SDA plates. The plates are incubated at 35° C. for 48 hours and yeast colonies are enumerated for determination of colony forming units (CFU) per gram of kidneys.

The compounds of the present invention may also be useful for inhibiting or alleviating *Pneumocystis carinii* infections in immune-comprised patients. The efficacy of the compounds of the present invention for therapeutic or anti-infective purposes may be demonstrated in studies on immunosuppressed rats.

Sprague-Dawley rats (weighing approximately 250 grams) are immunosuppressed with dexamethasone in the drinking water (2.0 mg/L) and maintained on a low protein diet for seven weeks to induce the development of pneumocystis pneumonia from a latent infection. Before drug treatment, rats are sacrificed to confirm the presence of *Pneumocystis carinii* pneumonia (PCP). Five rats (weighing approximately 150 grams) are injected twice, daily for four days subcutaneously (sc) with Compound in 0.25 ml of vehicle (distilled water). A vehicle control is also carried out. All animals continue to receive dexamethasone in the drinking water and low protein diet during the treatment period. At the completion of the treatment, all animals were sacrificed, the lungs are removed and processed, and the extent of disease determined by microscopic analysis of stained slides. The prevention or reduction of cysts are seen in slides of lungs of treated rats when compared with the number of cysts in lungs of untreated or solvent controls.

The outstanding properties are most effectively utilized when the compound is formulated into novel pharmaceutical compositions with a pharmaceutically acceptable carrier according to the conventional pharmaceutical compounding techniques.

The novel compositions contain at least a therapeutic antifungal or antipneumocystis amount of the active compound. Generally, the composition contains at least 1% by weight of Compound I. Concentrate compositions suitable for dilutions prior to use may contain 90% or more by weight. The compositions include compositions suitable for oral, topical, parenteral (including intraperitoneal, subcutaneous, intramuscular, and intravenous), nasal, and suppository administration, or insufflation. The compositions may be prepacked by intimately mixing Compound I with the components suitable for the medium desired.

Compositions formulated for oral administration may be a liquid composition or a solid composition. For liquid preparation, the therapeutic agent may be formulated with liquid carriers such as water, glycols, oils, alcohols, and the like, and for solid preparations such as capsules and tablets, with solid carriers such as starches, sugars, kaolin, ethyl cellulose, calcium and sodium carbonate, calcium phosphate, kaolin, talc, lactose, generally with lubricant such as calcium stearate, together with binders disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage. Compositions in unit dosage form constitute an aspect of the present invention.

Compositions may be formulated for injection and may take such forms as suspensions, solutions or emulsions in oily or aqueous vehicles such as 0.85 percent sodium chloride or 5 percent dextrose in water and may contain formulating agents such as suspending, stabilizing and/or dispersing agents. Buffering agents as well as additives such as saline or glucose may be added to make the solutions isotonic. The compound may also be solubilized in alcohol/propylene glycol or polyethylene glycol for drip intravenous administration. These compositions also may be presented in unit dosage form in ampoules or in multidose containers, preferable with added preservative. Alteratively, the active ingredients may be in powder form for reconstituting with a suitable vehicle prior to administration.

The term "unit dosage form" as used in the specification and claims refers to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of one of the compounds.

When the compound is for antifungal use any method of administration may be employed. For treating mycotic infections, oral or intravenous administration is usually employed.

When the compound is to be employed for control of pneumocystis infections it is desirable to directly treat lung and bronchi. For this reason inhalation methods are preferred. For administration by inhalation, the compounds of the present inventions are conveniently delivered in the form of an aerosol spray presentation from pressurized packs or nebulisers. The preferred delivery system for inhalation is a metered dose inhalation (MDI) aerosol, which may be formulated as a suspension or solution of Compound I in suitable propellants, such as fluorocarbons or hydrocarbons.

Although the compounds of the present invention may be employed as tablets, capsules, topical compositions, insufflation powders, suppositories and the like, the solubility of the compounds of the present invention in water and aqueous media render them adaptable for use in injectible formulations and also in liquid compositions suitable for aerosol sprays.

The following examples illustrate the invention but are not to be construed as limiting.

EXAMPLE 1

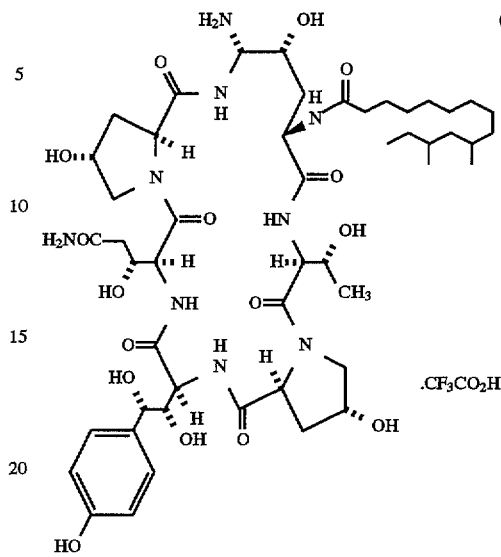

(Seq. ID No. 3)

Part A Preparation of Aminoethylthioether Intermediate (SEQ ID No. 15)

A solution of 500 milligrams (0.47 mmol) of 1-[4,5-dihydroxy-$N^2$-(10,12-dimethyl-1-oxotetradecyl)ornithine]-5-(3-hydroxyglutamine)-6-(4-hydroxyproline)echinocandin B, 5.34 grams (47 mmol) of 2-aminoethanethiol hydrochloride and 109 milligrams (0.47 mmol) of (1S)-(+)-10-camphorsulfonic acid in 40 milliliters of anhydrous N,N-dimethylformamide is stirred at 25° C. for 2–6 days or a period sufficient effect dissapearance of the starting material. The reaction is diluted with 40 milliliters of water and flash chromatographed on "LICHROPREP" (E. Merck) RP 18 (40–63 μm, 15 grams) packed in 10 percent acetonitrile/water. The column is eluted with 10 to 40 percent acetonitrile/water collecting two 120 milliliter fractions at each gradient step. The appropriate fractions, as determined by analytical HPLC (Zorbax Rx C18, 40% acetonitrile/water/0.1% trifluoroacetic acid, 210 nm) are concentrated and lyophilized. The residue is further purified by preparative HPLC (ZORBAX C18, 40% acetonitrile/water/0.1%TFA, 210 nm) to obtain the desired compound as a trifluroacetate salt with a molecular weight of 1238.

Part B Oxidation to Sulfone (SEQ ID No. 15)

The mixture of thioethers obtained as described above (0.358 mmol) is dissolved in 15 mL of 1:1 acetonitrile/water and "OXONE" (1.06 mmol equivalents of potassium hydrogen persulfate) is added. After about an hour, the solution is diluted with an equal volume of water and rapidly chromatographed using reverse phase C18 flash chromatography eluting with 35–45% acetonitrile/water containing 0.1% TFA in 2% step gradients. The product containing fractions are lyophilized to give the product with a molecular weight of 1270.

Part C Displacement of Sulfones with Azide (SEQ ID No. 21)

The mixture of sulfones (0.257 mmol), prepared as described above, is dissolved in 10 mL of anhydrous DMF. Lithium azide (0.257 mmol) is added as a solid and the mixture is stirred for about a 4–24 hours. The mixture is purified by reverse phase C18 flash chromatography eluting with 30–65% acetonitrile/water in 5% step gradients. The appropriate fractions, as determined by reverse phase HPLC (RP-18, 40% acetonitrile/water/0.1% TFA, 210 nm) are pooled, frozen and lyophilized to give the crude product. Further purification by preparative reverse phase HPLC (C18, 40–45% acetonitrile/water/0.1% TFA, 210 nm) yields the desired purified compound with a molecular weight of 1090.

Part D Reduction of Azide to Amine (SEQ ID No. 3)

A mixture of the azido compound (0.126 mmol) (obtained as described above) and 10% Pd on charcoal (100–150 mg) is suspended in glacial acetic acid (10 mL). The reaction vessel is flushed first with nitrogen then with hydrogen. One atmosphere pressure of hydrogen gas is maintained for a period of time sufficient to give complete reduction to the amine product, typically 2 to 24 h. The catalyst is removed by filtration and the filtrate is lyophilized to obtain the crude amine. Further purification may be accomplished by preparative reverse phase chromatography (C18, 35–41% acetonitrile/water/0.1% TFA in 3% step gradients, 210 nm). The product-containing fractions are lyophilized to give the purified compound with a molecular weight of 1178.

EXAMPLE 2

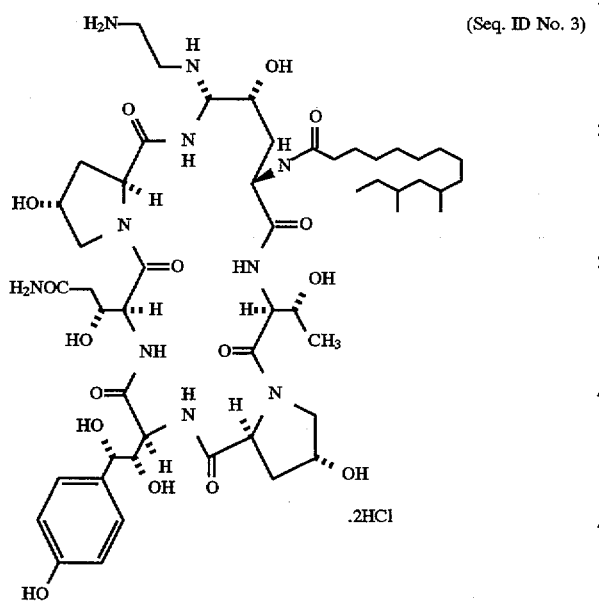

(Seq. ID No. 3)

The sulfone mixture (0.945 mmol), obtained as described in Part B Example 1, is dissolved in 20 mL of anhydrous DMF and ethylenediamine (9.45 mmol) is added. The mixture is stirred for about 1–12 hours or until analytical HPLC analysis (RP-18, 40% acetonitrile/water/0.1% TFA, 210 nm) shows complete disappearance of the starting sulfone. The mixture is separated by reverse phase (C18) flash column chromatography eluting with 10–40% acetonitrile/water/ 0.1%TFA in 5% step gradients. The appropriate fractions are pooled, frozen and lyophilized to give the desired product with the α-C-5 orn configuration and its β-C-5 orn epimer. The trifluoroacetate salt thus obtained is dissolved in a small volume of deionized water and passed throu a Bio-Rad AG2-X8 (Cl⁻) polyprep column washing with additional water. The product-containing eluate is lyophilized to give the desired product as the dihydrochloride salt with a molecular weight of 1180.

EXAMPLE 3

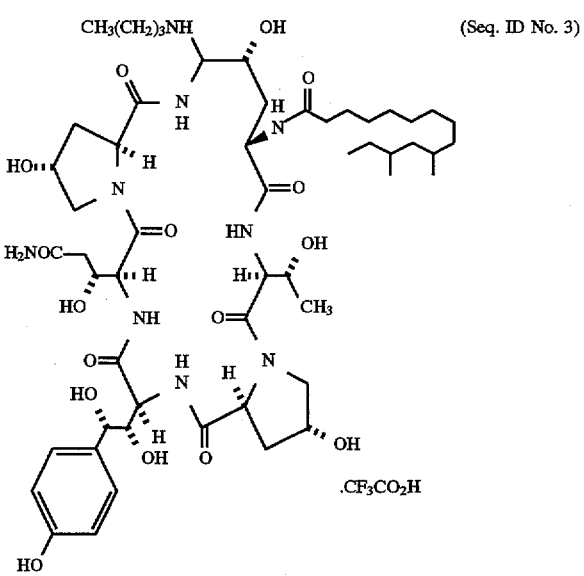

(Seq. ID No. 3)

The sulfone mixture (0.945 mmol), obtained as described in Part B Example 1, is dissolved in 20 mL of anhydrous DMF and n-butylamine (9.45 mmol) is added. The mixture is stirred for about 1–12 hours or until analytical HPLC analysis (RP-18, 40% acetonitrile/water/0.1% TFA, 210 nm) shows complete disappearance of the starting sulfone. The mixture is separated by reverse phase (C18) flash column chromatography eluting with 10–50% acetonitrile/water/ 0.1%TFA in 5% step gradients. The appropriate fractions are pooled, frozen and lyophilized to give the desired product with the α-C-5 orn configuration and its β-C-5 orn epimer. The products, isolated as their trifluoroacetate salts, have a molecular weight of 1234.

EXAMPLE 4

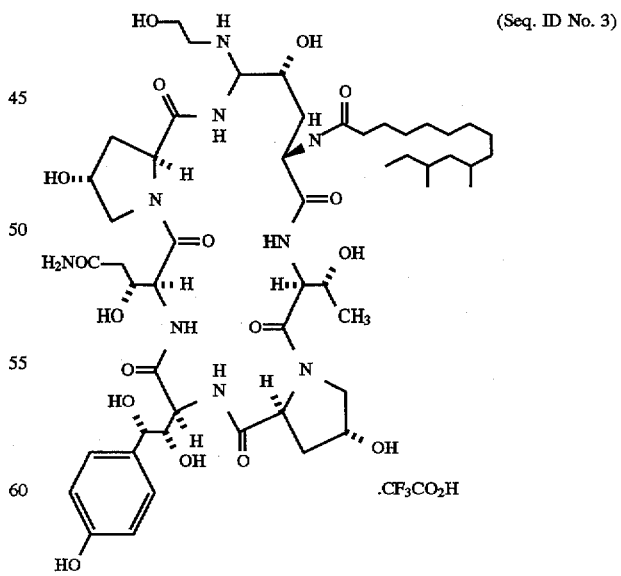

(Seq. ID No. 3)

The sulfone mixture (0.945 mmol), obtained as described in Part B Example 1, is dissolved in 20 mL of anhydrous DMF and ethanolamine (9.45 mmol) is added. The mixture is stirred for about 1–12 hours or until analytical HPLC analysis (RP-18, 40% acetonitrile/water/0.1% TFA, 210 nm) shows complete disappearance of the starting sulfone. The mixture is separated by reverse phase (C18) flash column chromatography eluting with 10–40% acetonitrile/water/ 0.1%TFA in 5% step gradients. The appropriate fractions are pooled, frozen and lyophilized to give the desired product with the α-C-5 orn configuration and a molecular weight of 1222.

EXAMPLE 5

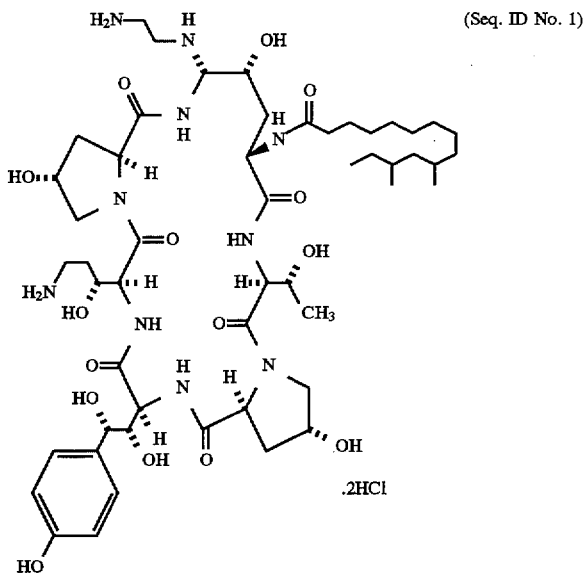

(Seq. ID No. 1)

Part A Preparation of Intermediate Nitrile Compound (SEQ ID No. 2)

A solution of 250 milligrams (0.23 mmol) of 1-[4,5-dihydroxy-$N^2$-(10,12-dimethyl-1-oxotetradecyl)ornithine]-5-(3-hydroxyglutamine)-6-(4-hydroxyproline)echinocandin B was prepared in 3.0 mL of N,N-dimethylformamide. In one portion 64 milligrams of cyanuric chloride was added and the mixture was stirred for 5.5 minutes and immediately quenched with 0.55 mL of 2M sodium acetate solution. The mixture was purified by preparative HPLC ("ZORBAX" C8, acetonitrile/water/0.1% TFA, 210 and 277 nm). The appropriate product-containing fractions as determined by analytical HPLC ("ZORBAX" C8, 45% water/acetonitrile/0.1% TFA, 1.5 mL/min, 210 and 277 nm) were pooled and lyophilized to give 45 mg of desired nitrile compound>98% pure as a white solid. $^1$H NMR (400 MHz, $CD_3OD$) δ7.12 (d, 1H), 6.74 (d, 1H), 5.31 (m, 1H), 2.83 (dd, 1H), 2.72 (dd, 1H), 2.42 (m, 1H), 1.21 (d, 3H); FAB-MS (Li), m/e 1054 (M+H+Li).

Part B Reduction of Nitrile to Amine (SEQ ID No. 1)

To a solution of 38.5 mg (0.036 mmol) of the nitrile (prepared above in Part A) in 2.0 mL of methanol, was added 32 mg (0.25 mmol) of $CoCl_2 \cdot 6$ $H_2O$. Next, 46 mg (34 equivalents) of sodium borohydride was added in several portions. The micture was stirred under a nitrogen atmosphere at room temperature for 3 hours. The reaction mixture was purified by preparative HPLC ("ZORBAX" C8, 45% water/acetonitrile, 210 and 277 nm). The appropriate fractions as determined by analytical HPLC ("ZORBAX" C8, 45% water/acetonitrile/0.1% TFA, 1.5 mL/min, 210 and 277 nm) were pooled and lyophilized to give 13 mg of the trifluoroacetate salt of the desired amine (>98% pure) as a white solid. FAB-MS (Li), m/e 1058 (M+H+Li).

Part C Preparation of the Aminoethylthioether (SEQ ID No. 13)

A solution of the amine prepared in Part B above (0.047 mmol), 2-aminoethanethiol hydrochloride (4.7 mmol) and (1S)-(+)-10-camphorsulfonic acid (0.047 mmol) in 4 milliliters of anhydrous N,N-dimethylformamide is stirred at 25° C. for 2–6 days or a period sufficient effect dissapearance of the starting material. The reaction is diluted with 4 milliliters of water and flash chromatographed on "LICHROPREP" (E. Merck) RP 18 (40–63 μm, 1.5 grams) packed in 10 percent acetonitrile/water. The column is eluted with 10 to 40 percent acetonitrile/water collecting two 12 milliliter fractions at each gradient step. The appropriate fractions, as determined by analytical HPLC (Zorbax Rx C18, 30% acetonitrile/water/0.1% trifluoroacetic acid, 210 nm) are concentrated and lyophilized. The residue is further purified by preparative HPLC (ZORBAX C18, 30% acetonitrile/water/0.1%TFA, 210 nm) to obtain the desired isomeric compounds as ditrifluoroacetate salts both having molecular weights of 1338.

Part D Oxidation to Sulfone (SEQ ID No. 13)

The mixture of thioethers obtained as described above (0.036 mmol) is dissolved in 1.5 mL of 1:1 acetonitrile/water and "OXONE" (0.106 mmol equivalents of potassium hydrogen persulfate) is added. After about an hour, the solution is diluted with an equal volume of water and rapidly chromatographed using reverse phase C18 flash chromatography eluting with 35–45% acetonitrile/water containing 0.1% TFA in 2% step gradients. The product-containing fractions are lyophilized to give the product with a molecular weight of 1370.

Part E Displacement of Sulfone with Ethylenediamine (SEQ ID No. 1)

The sulfone mixture (0.094 mmol), obtained as described in Part D above, is dissolved in 2.0 mL of anhydrous DMF and ethylenedime (0.94 mmol) is added. The mixture is stirred for about 1–12 hours or until analytical HPLC analysis (RP-18, 30% acetonitrile/water/0.1% TFA, 210 nm) shows complete disappearance of the starting sulfone. The mixture is separated by reverse phase (C18) flash column chromatography eluting with 10–30% acetonitrile/water/ 0.1%TFA in 5% step gradients. The appropriate fractions are pooled, frozen and lyophilized to give the desired product with the α-C-5 orn configuration and its β-C-5 orn epimer. The trifluoroacetate salt thus obtained is dissolved in a small volume of deionized water and passed throu a Bio-Rad AG2-X8 ($Cl^-$) polyprep column washing with additional water. The product-containing eluate is lyophilized to give the desired product as the dihydrochloride salt with a molecular weight of 1166.

EXAMPLE 6

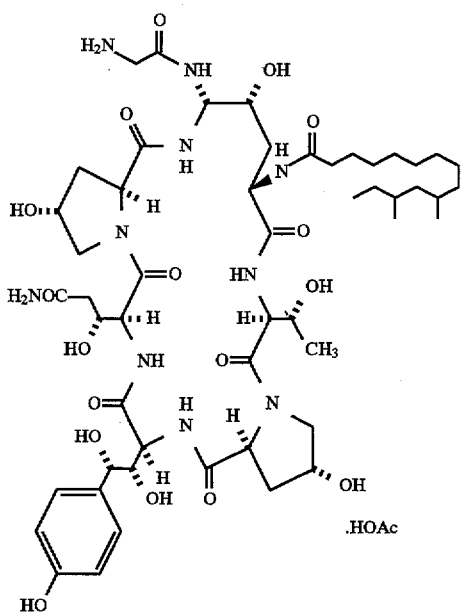

(Seq. ID No. 3)

.HOAc

Part A Acylation with Protected Glycine

The amino compound (0.10 mmol), obtained in Example 1 Part D, is dissolved in 1 mL of anhydrous N,N-dimethylformamide under a nitrogen atmosphere. Diisopropylethylamine (0.11 mmol) and N-Carbobenzyloxyglycine pentafluorophenyl ester (0.15 mmol) are added and the reaction is stirred at room temperature for 1–12 hours or until analysis by analytical HPLC ("ZORBAX" C18, 50% acetonitrile/water/0.1% TFA, 210 and 277 nm) indicates the reaction is complete. The mixture is diluted with 1 mL of methanol and purified by preparative HPLC ("ZORBAX" C18, 70% water/acetonitrile/0.1% TFA to 50% water/acetonitrile/0.1% TFA, 2 step gradient, 210 and 277 nm) to give the desired glycylated compound with a molecular weight of 1255.

Part B Hydrogenolysis of Carbobenzyloxy Protected Glycine Compound

The pure carbobenzyloxy-protected compound (0.075 mmol) obtained as in Part A above, is dissolved in a mixture of 3 mL of methanol, 1 mL of water and 0.2 mL of glacial acetic acid. Next, 50 mg of 10% palladium on charcoal is added and the reaction vessel is flushed first with nitrogen, then hydrogen. The reaction is stirred rapidly under 1 atmosphere of hydrogen for several hours. The catalyst is removed by filtration and the volatiles are removed by rotary evaporation under reduced pressure. The residue is dissolved in 2 mL of water, frozen and lyophilized to give the desired deprotected amine product as a solid. The desired product has a molecular weight of 1181.

EXAMPLE 7

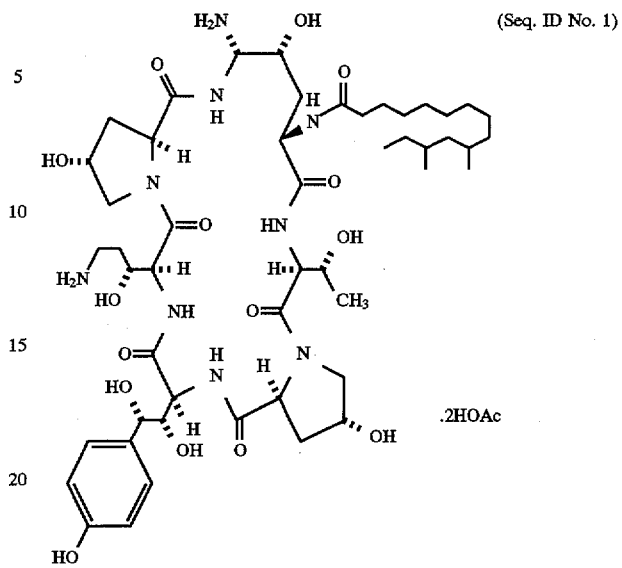

(Seq. ID No. 1)

.2HOAc

Part A Displacement of Sulfones with Azide (SEQ ID No. 19)

The mixture of sulfones (0.257 mmol), prepared as described in Part D of Example 5, is dissolved in 10 mL of anhydrous DMF. Lithium azide (0.257 mmol) is added as a solid and the mixture is stirred for about a 4–24 hours. The mixture is purified by reverse phase C18 flash chromatography eluting with 20–55% acetonitrile/water in 5% step gradients. The appropriate fractions, as determined by reverse phase HPLC (RP-18, 40% acetonitrile/water/0.1% TFA, 210 nm) are pooled, frozen and lyophilized to give the crude product. Further purification by preparative reverse phase HPLC (C18, 30–40% acetonitrile/water/0.1% TFA, 210 nm) yields the desired purified compound with a molecular weight of 1190.

Part B Reduction of Azide to Amine (SEQ ID No. 1)

A mixture of the azido compound (0.126 mmol) (obtained as described above in Part A) and 10% Pd on charcoal (100–150 mg) is suspended in glacial acetic acid (10 mL). The reaction vessel is flushed first with nitrogen then with hydrogen. One atmosphere pressure of hydrogen gas is maintained for a period of time sufficient to give complete reduction to the amine product, typically 2 to 24 h. The catalyst is removed by filtration and the filtrate is lyophilized to obtain the desired amine as a diacetate salt with a molecular weight of 1170.

EXAMPLE 8

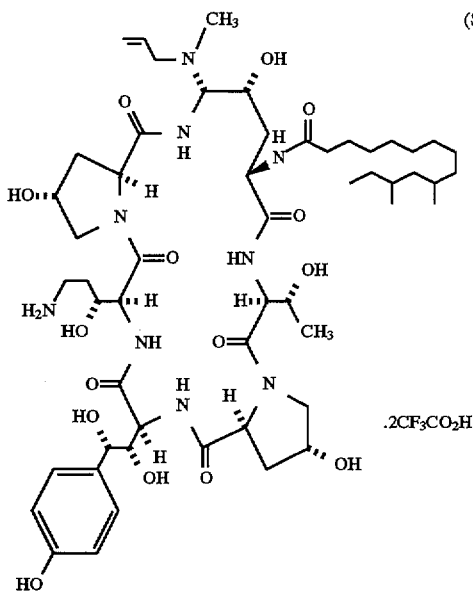

(Seq. ID No. 1)

The sulfone mixture (0.094 mmol), obtained as described in Part D Example 5, is dissolved in 2.0 mL of anhydrous DMF and N-methyl-N-allylamine (0.945 mmol) is added. The mixture is stirred for about 1–12 hours or until analytical HPLC analysis (RP-18, 40% acetonitrile/water/0.1% TFA, 210 nm) shows complete disappearance of the starting sulfone. The mixture is separated by reverse phase (C18) flash column chromatography eluting with 10–40% acetonitrile/water/0.1%TFA in 5% step gradients. The appropriate fractions are pooled, frozen and lyophilized to give the desired product with the α-C-5 orn configuration and a molecular weight of 1332.

EXAMPLE 9

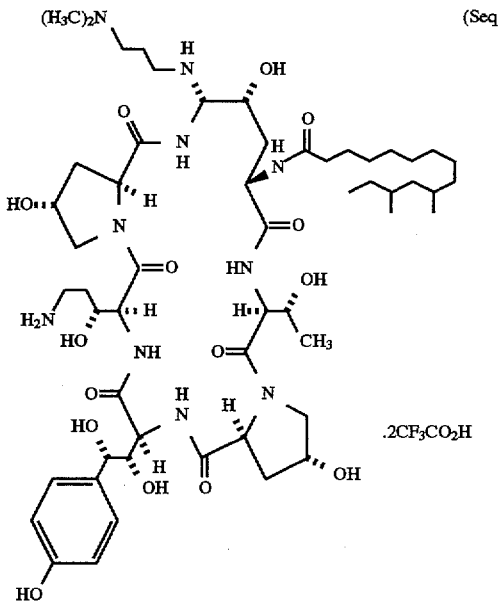

(Seq. ID No. 1)

The sulfone mixture (0.094 mmol), obtained as described in Part D Example 5, is dissolved in 2.0 mL of anhydrous DMF and N,N-dimethylethyl-1,3-diaminopropane (0.945 mmol) is added. The mixture is stirred for about 1–12 hours or until analytical HPLC analysis (RP-18, 40% acetonitrile/water/0.1% TFA, 210 nm) shows complete disappearance of the starting sulfone. The mixture is separated by reverse phase (C18) flash column chromatography eluting with 10–40% acetonitrile/water/0.1%TFA in 5% step gradients. The appropriate fractions are pooled, frozen and lyophilized to give the desired product with the α-C-5 orn configuration and a molecular weight of 1363.5.

The following examples illustrate representative compositions containing the compounds of the invention.

EXAMPLE A 1000 compressed tablets each containing 500 mg of the compound of Example 5 are prepared from the following formulation:

| Compound | Grams |
|---|---|
| Compound of Example 5 | 500 |
| Starch | 750 |
| Dibasic calcium phosphate, hydrous | 5000 |
| Calcium stearate | 2.5 |

The finely powdered ingredients are mixed well and granulated with 10 percent starch paste. The granulation is dried and compressed into tablets.

EXAMPLE B 1000 hard gelatin capsules, each containing 500 mg of the same compound are prepared from the following formulation:

| Compound | Grams |
|---|---|
| Compound of Example 5 | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE C

An aerosol composition may be prepared having the following formulation:

|  | Per Canister |
|---|---|
| Compound of Example 5 | 24 mg |
| Lecithin NF Liquid Concd. | 1.2 mg |
| Trichlorofluoromethane, NF | 4.026 g |
| Dichlorodifluoromethane, NF | 12.15 g |

EXAMPLE D 250 milliliters of an injectible solution may be prepared by conventional procedures having the following formulation:

| | |
|---|---|
| Dextrose | 12.5 g |
| Water | 250 ml |
| Compound of Example 5 | 400 mg |

The ingredients are blended and thereafter sterilized for use.

Preparation of Starting Materials

The starting material, Compound A-3 Seq. ID No. 3, in which $R^1$ is 9,11-dimethyltridecyl may be produced by cultivating a mutagenized form of *Zalerion arboricola* ATCC 20868 as described in U.S. Pat. No. 5,306,708 which issued on Apr. 26, 1994.

Starting materials in which $R^I$ is a different group from that of the natural product may be obtained by deacylating the lipophilic group of the natural product by subjecting the natural product in a nutrient medium to a deacylating enzyme until substantial deacylation occurs, the enzyme having first been obtained by cultivating a microorganism of the family pseudomondaceae or actinoplanaceae, as described in Experentia 34, 1670 (1978) or U.S. Pat. No. 4,293,482. The deacylated cyclopeptide is recovered and thereafter reacylated by mixing together with an appropriate active ester RCOZ where Z is halogen, pentachlorophenoxy, pentafluorophenoxy, p-nitrophenoxy and the like, to obtain compound a with the desired acyl group.

---

What is claimed is:

1. A compound of the formula (Seq. ID No. 1)

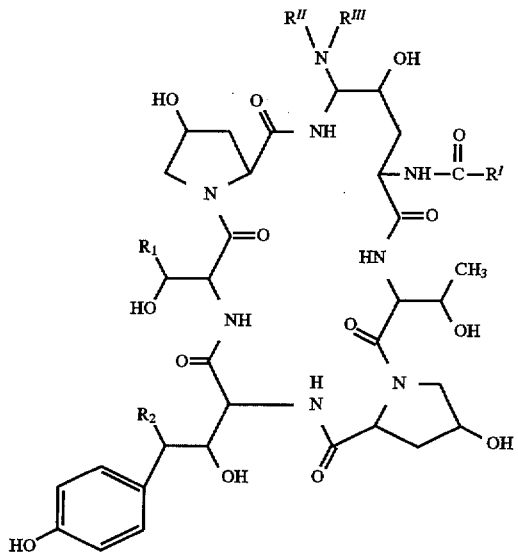

(I)

wherein $R^1$ is $CH_2CH_2NH_2$;

$R_2$ is OH;

$R^I$ is 9,11-dimethyltridecyl;

$R^{II}$ is $CH_2CH_2NH_2$; and $R^{III}$ is hydrogen; or a pharmaceutically acceptable acid addition salt thereof.

2. An antibiotic composition comprising an effective amount of the compound as defined in claim 1 in a pharmaceutically acceptable carrier.

3. A composition according to claim 2 in unit dosage form wherein the compound is present in an amount of about 10 to 200 milligrams.

* * * * *